United States Patent
Song et al.

(10) Patent No.: US 7,171,192 B2
(45) Date of Patent: Jan. 30, 2007

(54) PORTABLE WIRELESS DATA DEVICE

(75) Inventors: Li Song, Mounds View, MN (US); Jia Hu, Mounds View, MN (US)

(73) Assignee: Galleria Industrial Company, Mounds View, MN (US)

( * ) Notice: Subject to any disclaimer, the term of this patent is extended or adjusted under 35 U.S.C. 154(b) by 759 days.

(21) Appl. No.: 10/407,654

(22) Filed: Apr. 4, 2003

(65) Prior Publication Data

US 2004/0198438 A1 Oct. 7, 2004

(51) Int. Cl.
*H04M 3/42* (2006.01)
*H04B 1/38* (2006.01)

(52) U.S. Cl. .............................. 455/414.3; 455/556.1; 455/556.2

(58) Field of Classification Search ................ 345/1.1, 345/169; 455/414.3, 556.1, 556.2; 705/15, 705/27
See application file for complete search history.

(56) References Cited

U.S. PATENT DOCUMENTS

| | | | |
|---|---|---|---|
| 5,003,472 A | 3/1991 | Perrill et al. ................ 364/401 |
| 5,054,112 A | 10/1991 | Ike ............................. 455/41 |
| 5,629,499 A | 5/1997 | Flickinger et al. ............ 178/18 |
| 5,845,263 A | 12/1998 | Camaisa et al. .............. 705/27 |
| 6,257,486 B1 | 7/2001 | Teicher et al. .............. 235/380 |
| 6,273,335 B1 | 8/2001 | Sloan ......................... 235/382 |
| 6,313,828 B1 | 11/2001 | Chombo ..................... 345/169 |
| 6,380,928 B1 | 4/2002 | Todd .......................... 345/169 |
| 6,384,850 B1 | 5/2002 | McNally et al. ............. 345/810 |
| 6,405,167 B1 | 6/2002 | Cogliano .................... 704/251 |
| 6,493,734 B1 | 12/2002 | Sachs et al. ................. 707/526 |
| 6,512,497 B1 | 1/2003 | Kondo et al. ................. 345/1.1 |
| 6,529,185 B1 | 3/2003 | Armstrong ................. 345/159 |
| 6,650,867 B2 | 11/2003 | Redford et al. ............. 434/307 |
| 2002/0138350 A1 | 9/2002 | Cogen ......................... 705/15 |
| 2002/0147647 A1 | 10/2002 | Ragsdale-Elliott et al. ... 705/15 |
| 2002/0197588 A1 | 12/2002 | Wood et al. ................. 434/185 |

FOREIGN PATENT DOCUMENTS

WO    WO 98/41963    9/1998

*Primary Examiner*—Bing Q. Bui
(74) *Attorney, Agent, or Firm*—Brooks & Cameron, PLLC

(57) ABSTRACT

Systems, methods, and devices are provided which include a portable wireless data device. One embodiment of the portable wireless data device includes one or more physical pages. An array of inputs is embedded in the one or more pages. A wireless transceiver is operably coupled to the array of inputs. One or more text sections are provided on a face of the one or more pages.

38 Claims, 7 Drawing Sheets

PORTABLE WIRELESS DATA DEVICE

INTRODUCTION

Filling out paper form questionnaires is a regular part of everyone's daily life. Real-life events from ordering food in restaurants, updating medical histories in hospitals and clinics, to election ballots in national and local elections, are all done by providing formatted information for selection, e.g. questions and answers. Posing questions and recording answers is also performed in the process of surveys. Similarly, surveys involve the formatting of questions and selections for response.

Electronic media and device technology has begun to replace printed text media in many applications. This includes the occurrence of wired electronic survey devices. However, such wired electronic survey devices require systems with computer screens, either touch screen or flat panel, as a human interface and another computer workstation running in the background to process the information. Such systems can be large and costly, requiring a dedicated infrastructure. Moreover, individuals may have to modify their traditional behavior in various settings in order to interact with new media and devices.

Wireless technology, including wireless mobile computing in the form of laptops and Personal Digital Assistants (PDA's), has proliferated in recent years. However, in certain instances and/or settings, e.g. restaurants and health clinics, laptops can be too cumbersome to use for presenting information and gathering responses. Multifunction handheld devices such as cell phones, PDAs, and the like accommodate the wireless transfer of information between devices. However, such devices often do not provide sufficiently large enough screens to support a user-friendly presentation of copious information at one time or at a glance. Moreover, for the technologically adverse individual, added gadgets and devices may present an annoyance or require additional instruction for use.

DETAILED DESCRIPTION

Figure 1:
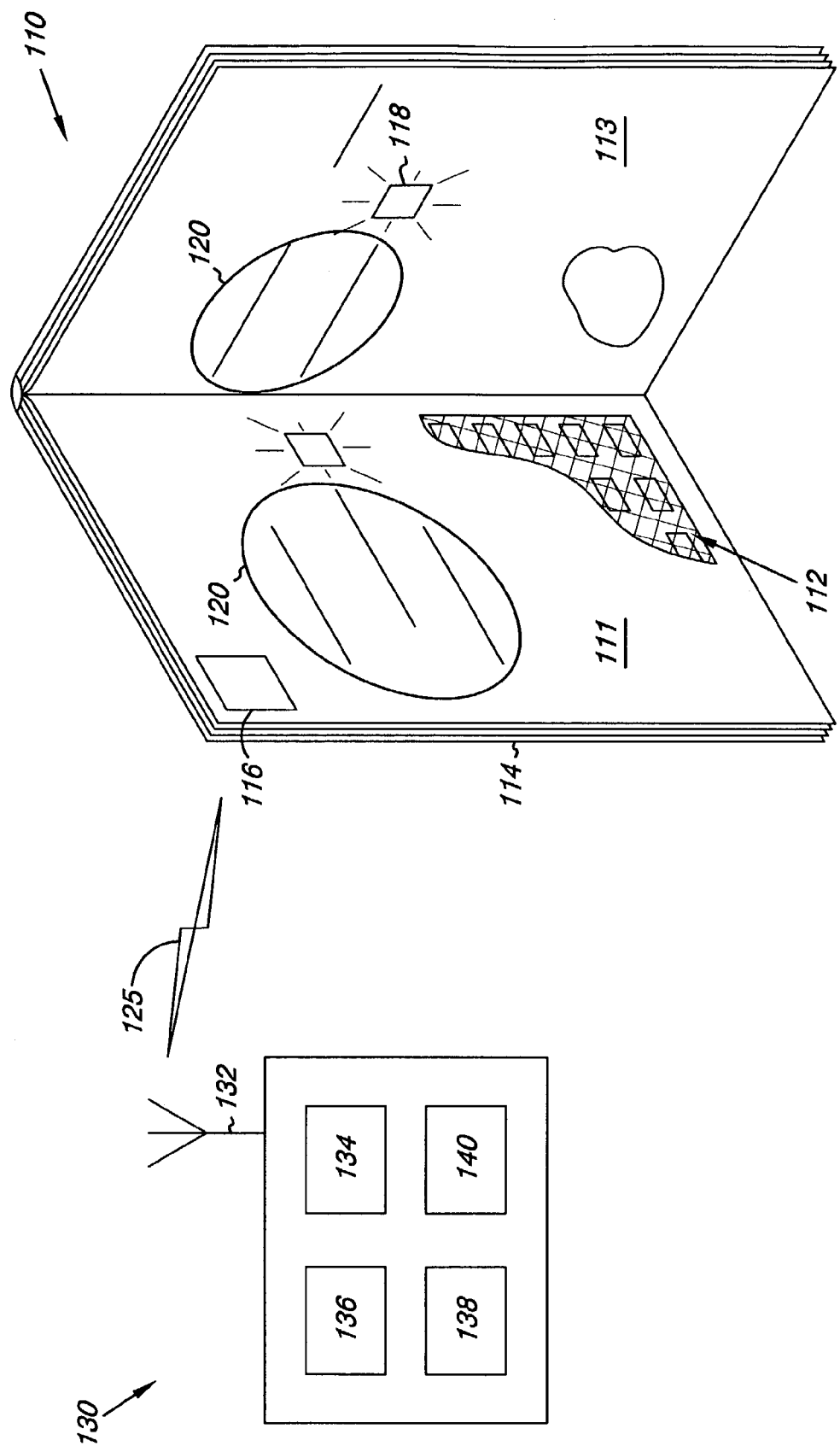
FIG. 1 illustrates an embodiment of a wireless information gathering architecture.

Embodiments of the present invention provide for the integration of printed text information with the advantages of wireless capability. Individuals who prefer or are more comfortable with a paper form of Q&A, or menus that they can hold in their hands while they read, can still capitalize on the benefits of wireless electronic data transfer. By way of example and not by way of limitation, sheet or paper format, portable wireless devices are provided which can be used in such settings as restaurant menu item selection, medical information collection, surveys and voting events.

As one of ordinary skill in the art will understand upon reading this disclosure, embodiments of the invention can be performed by software, application modules, and computer executable instructions operable on the systems and devices shown herein or otherwise. The invention, however, is not limited to any particular operating environment or to software written in a particular programming language. Software, application modules and/or computer executable instructions, suitable for carrying out embodiments of the present invention, can be resident in one or more devices or locations or in several and even many locations.

One of ordinary skill in the art will appreciate that various components and/or devices described herein can include a computer readable medium, on which a set of computer executable instructions can reside. There are many forms of computer readable medium, including Flash memory, RAM, ROM, DDRAM, and the like, which can be included in one and/or all of the various components mentioned, or within a multifunction device.

Unless explicitly stated, the method embodiments described herein are not constrained to a particular order or sequence. Additionally, some of the described method embodiments can occur or be performed at the same point in time.

In certain commercial and industrial markets, bar-code technology or other printed labels are used for automated data management, ordering and data entry. Bar codes and/or printed labels can be inexpensive and as such have become widely used. However, bar-codes have to be printed and configured in conjunction with particular applications. Additionally, there is not an easy way to convert real-time data into bar-code labels in point of sale applications and/or point of use applications (e.g. "on the fly" entries). Another approach that can be used for automated data management, ordering, and data entry include punched cards/slips. However, this approach suffers from similar shortcomings to that of bar-codes in addition to requiring hole punching tools and equipment.

As stated above, the use of PDA's, with high-speed data wireless communication standards such as "Blue Tooth" technology, are becoming more and more prevalent in the market place. However, PDA's with such capability can be expensive and are over-engineered for some data management, ordering and data entry. In such instances, these wireless handheld devices provide a low value-to-cost ratio.

Therefore, embodiments of the present invention are designed to efficiently harmonize the integration of printed text information with the advantages of wireless capability such that individuals who prefer or are more comfortable with a paper form of Q&A or menus that they can hold in their hands, and read in large format, can still capitalize on the benefits of wireless electronic data transfer.

FIG. 1 illustrates an embodiment of a wireless information gathering architecture 100. As shown in the embodiment of FIG. 1, the architecture includes a portable wireless data device 110. In various embodiments, the portable wireless data device 110 includes an array of selection inputs (shown in a cut-away view 112) within a sheet format housing 114. As used herein, a sheet format housing is intended to include both rigid, semi-rigid, and fully pliable materials having dimensions generally associated with the size and shape of a sheet of paper or menu card. By way of example and not by way of limitation, the sheet format housing can have dimensions of approximately 8½ inches by 11 inches by less than a ¼ inch in thickness. In various embodiments, the sheet format housing is a cellulose based housing. However, the sheet format housing can be made from a plastic material or laminate with the array of selection inputs 112 embedded or laminated inside. The invention is not limited to the particular materials or dimensions stated above.

In the embodiment shown in FIG. 1, the portable wireless data device includes a foldable format with a first interior face 111 and a second interior face 113 closeable upon one another. The invention, however, is not so limited and can consist of an individual sheet format housing. In the embodiment of FIG. 1, each interior face 111 and 113 includes an array of selection inputs 112 within a sheet format housing 114.

As shown in the embodiment of FIG. 1, the portable wireless data device includes one or more visual indicators 118 operably coupled to the array of selection inputs. And, as shown in FIG. 1, one or more sections of text 120 are printable on the sheet format housing 114. In various embodiments, at least one section of printed text is associated with a selection input among the array of selection inputs 112.

A transceiver 116 is operably coupled to the array of selection inputs 112. In various embodiments, the transceiver includes a radio frequency identification (RFID) chip component. And, in various embodiments, the RFID includes a dual interface RFID having a contact interface and a contact-less or wireless interface. The invention, however, is not so limited. The transceiver is operable to communicate radio frequency (RF) signals 125 with a remote terminal 130. By way of example and not by way of limitation, the remote terminal 130 can include an access point (AP) in a packet-switched Internet protocol (IP) environment or a base station such as in circuit-switch cellular network environment.

In the embodiment of FIG. 1, a workstation remote terminal 130 is illustrated which includes an antenna 132 for receiving the RF signals. As one or ordinary skill in the art will appreciate, the workstation 130 can include a processor or application modules 134, a memory 136, a display 138, and a printing device 140.

Figure 2A:
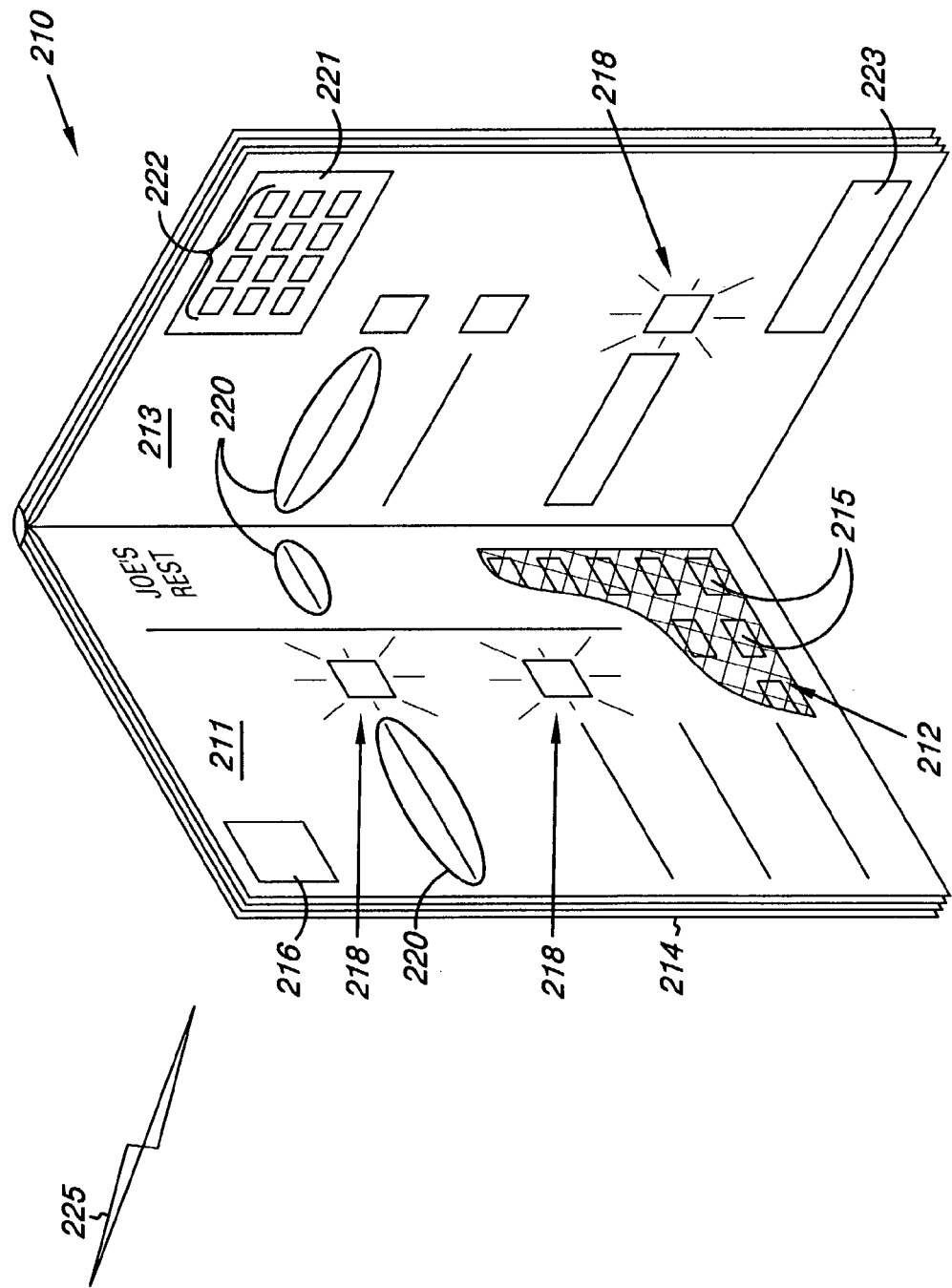
FIG. 2A illustrates an embodiment for a portable wireless data device.

FIG. 2A illustrates an embodiment for a portable wireless data device 210 as suited to gathering information such as menu selection items and/or survey selection responses. As shown in the embodiment of FIG. 2A, the portable wireless data device includes a foldable format with a first interior face 211 and a second interior face 213 closeable upon one another. As described above each interior face, 211 and 213 includes an array of selection inputs 212 within a sheet format housing 214. In various embodiments, the sheet-like format housing includes a membrane switch (shown in a cut-away view as 212). As before, the device 210 includes a transceiver 216. In various embodiments, the transceiver 216 includes a radio frequency identification (RFID) chip operably coupled to the membrane switch. In various embodiments, the RFID chip includes a dual interface RFID chip having a contact interface and a wireless interface.

Figure 2B:
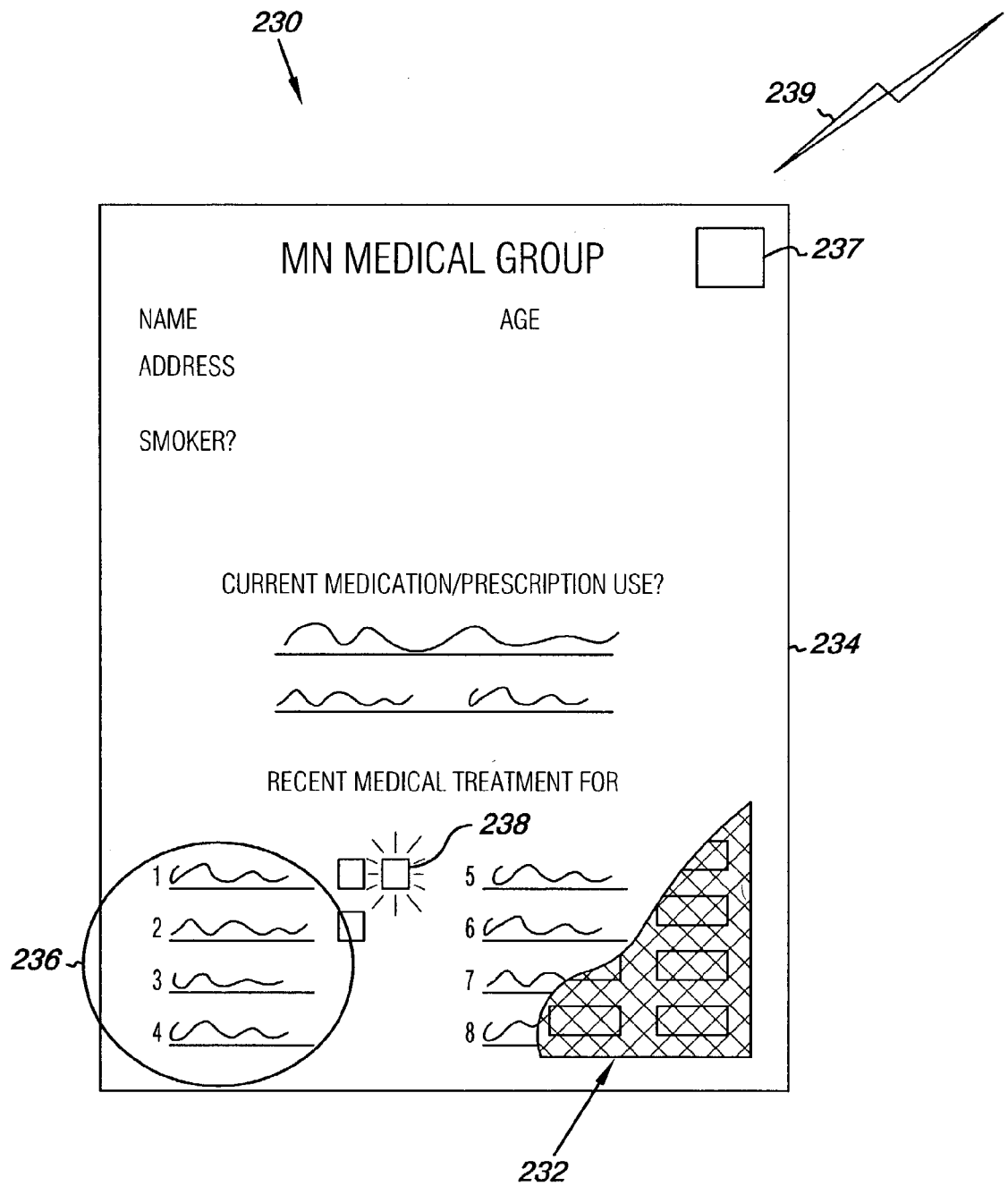
FIG. 2B illustrates another embodiment for a portable wireless data device.
Figure 2C:
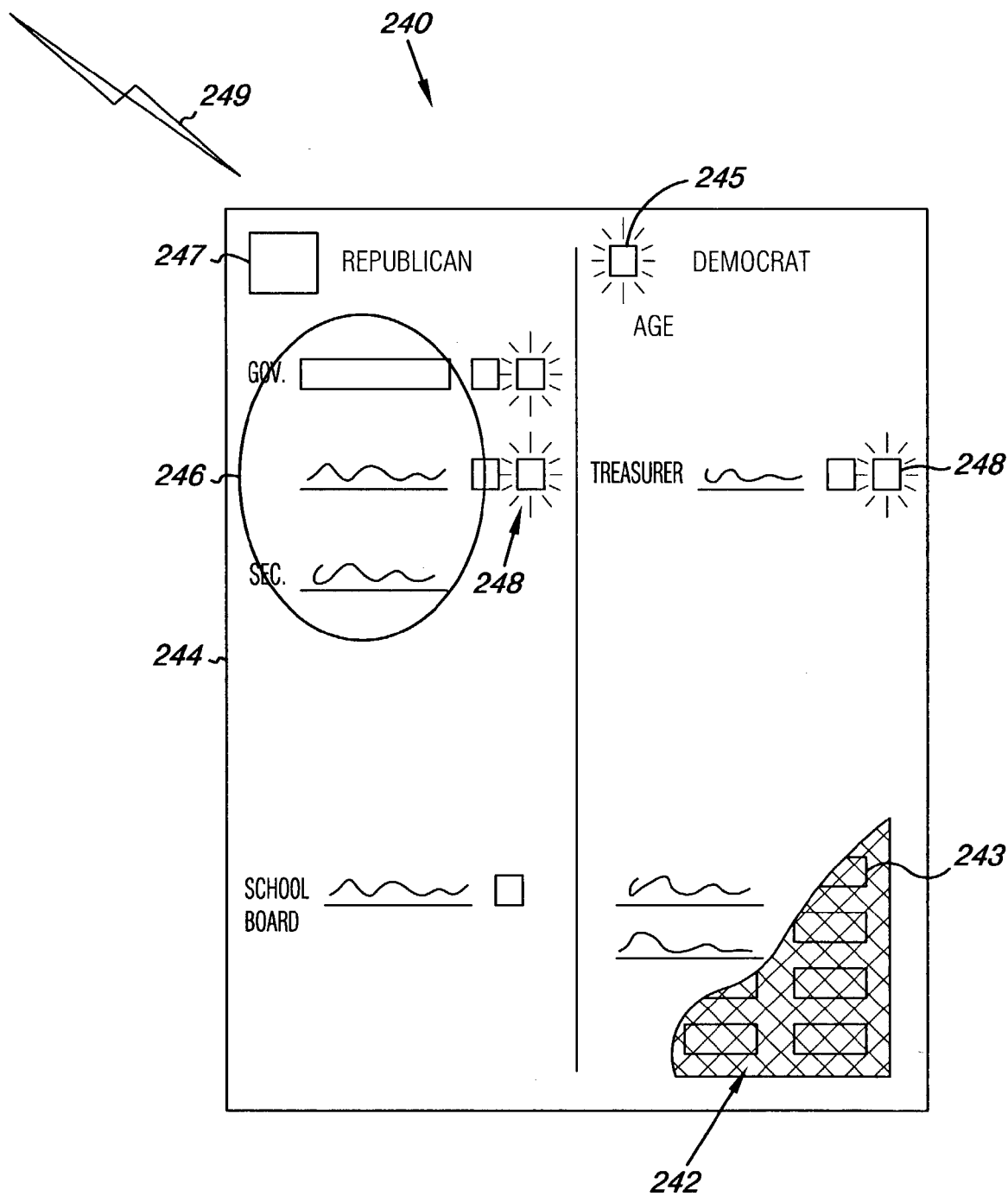
FIG. 2C illustrates another embodiment for a portable wireless data device.

As shown in the embodiment of FIG. 2A, the device 210 includes one or more visual indicators 218 operably coupled to the membrane switch. The embodiment of FIG. 2A, illustrates a sheet-like format housing 214 having one or more sections of printed text 220 thereon. In various embodiments, the sheet-like format housing includes a paper housing having one or more sections of printed text thereon. As one of ordinary skill in the art will appreciate upon reading this disclosure the one or more sections of printed text can include printed text as suited for gathering particular information. For example, the printed text can be selected from the group of restaurant menu items, political office candidates, and medical history questions depending on the particular purpose or use of the device 210. In the embodiment of FIG. 2A, restaurant menu items are provided. FIGS. 2B and 2C include the components described in connection with FIG. 2A. In the embodiment of FIG. 2B, the one or more sections of printed text pertain to medical questions. And, in the embodiment of FIG. 2C, the one or more sections of printed text pertain to political office candidates.

As shown in the embodiment of FIG. 2A, a membrane switch 212 includes one or more selectable option input points 215. In various embodiments, one or more input points 215 can be associated with a particular section of printed text. As described in more detail below, not all of the one or more input points 215 available have to be employed in any particular application.

In various embodiments, as shown in FIG. 2A, one or more visual indicators 218 can be associated with an input point and can be triggered by, and/or actuable in response to, contact or selection of an input point 215. Not all of the one or more visual indicators 218 available have to be employed in any particular application. In various embodiments, the one or more visual indicators can include light emitting diodes (LEDs). However, the invention is not so limited.

As will be discussed in more detail in connection with FIG. 3, the devices, 210, 230 and 240, shown in FIGS. 2A–2C can further include a processor operably coupled to the membrane switch, visual indicators and the RFID chip. The devices 210, 230 and 240 can include a memory operably coupled to the processor. And, as shown in the embodiment of FIG. 2A, the device can include an input section 221 having one or more input keys 222. In some embodiments, a device can further include a display 223 and power source (not shown) operably coupled to the processor.

In various embodiments discussed below, the sheet format housing includes at least one area available to physically write text or to post/attach labels to be associated with a selection input. And, in various embodiments, a portable wireless data device is provided with an audio functionality. That is, an audio chip (shown in FIG. 3) can be interfaced with the array of selection inputs 212. In such embodiments, the audio functionality is operable to provide audio information upon actuation of a selection input. In various embodiments, the audio information can includes a summary or description of a selection input. And, in various embodiments, the audio information can provide a summary of an entire transaction upon user indication of selection completion.

Figure 3:
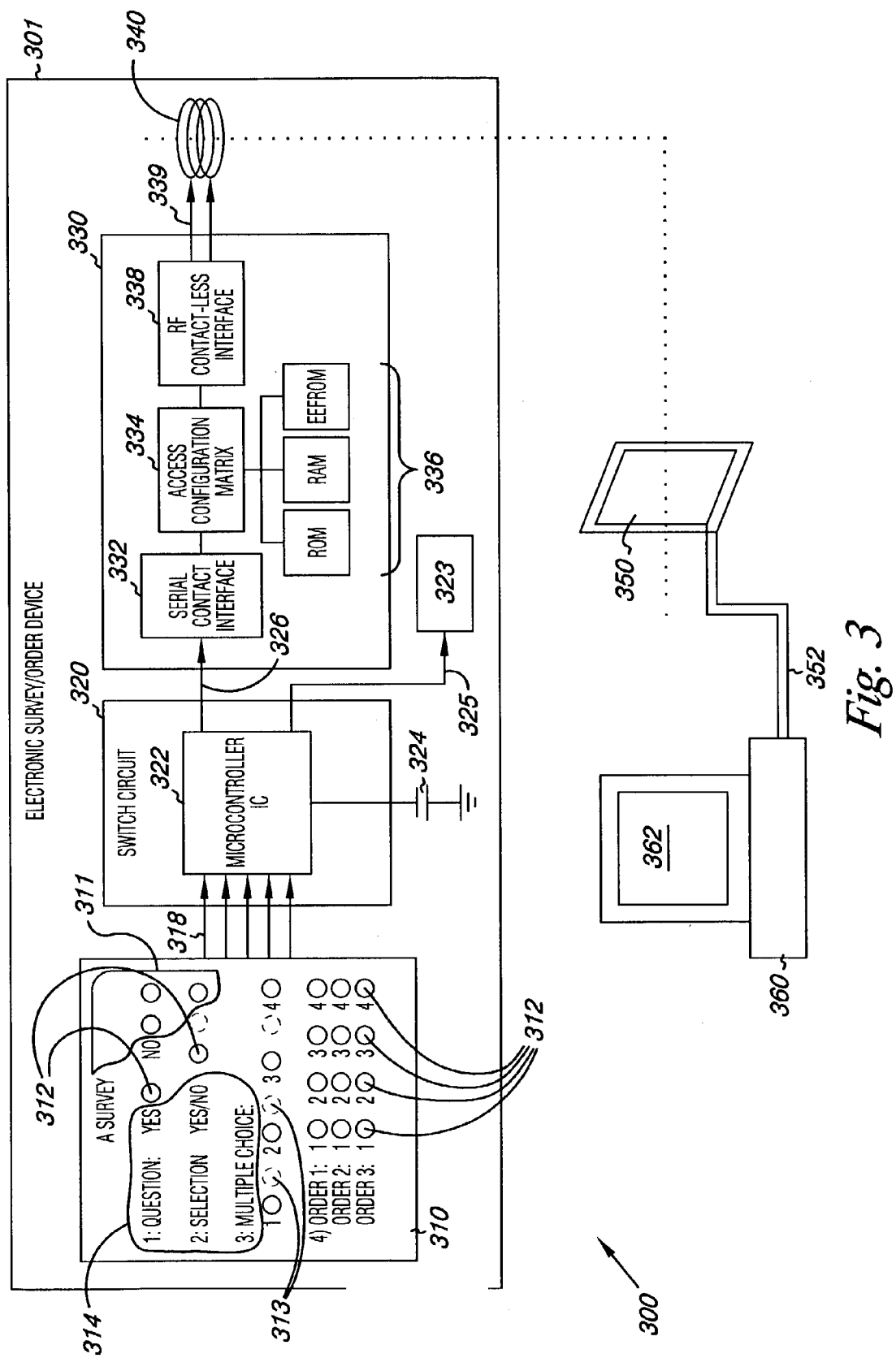
FIG. 3 illustrates an architecture, interface, and electrical components associated with an embodiment of the present invention.

FIG. 3 illustrates an architecture, interface, and electrical components 300 associated with an embodiment of the present invention. As shown in the embodiment of FIG. 3, a portable wireless data device 301 includes one or more physical pages/sheets 310. Page 310 has a face or a cover, or even a sleeve 310. The one or more physical pages/sheets 310 include an array matrix of inputs (shown in cut-away view 311) provided on a substrate embedded in the physical pages/sheets 310. Also embedded in the portable wireless data device 301 are a switch circuit 320, a wireless integrated circuit (IC) 330, an antenna 340, and a power source (such as a battery) 324. As one of ordinary skill in the art will appreciate upon reading this disclosure, other operational components can additionally be embedded in the portable wireless data device 301.

As shown in the embodiment of FIG. 3, certain ones, or a first set, 312 of the inputs 311 are viewable or represented on the physical pages/sheets 310 while other ones, or a second set, 313 are obstructed or concealed from view on the physical pages/sheets 310. As one of ordinary skill in the art will appreciate upon reading this disclosure, in various embodiments the inputs 311 can be selectively enabled or activated such that only certain ones of the inputs 311 are activated or actuable for a given use or application. That is, by way of example and not by way of limitation, in various embodiments a subset, e.g. the first set 312 of inputs 311 which are viewable or represented on the physical pages/sheets 310, are activated and operable to register input, while another subset, e.g. the second set 313 of inputs which are obstructed or concealed from view on the physical pages/sheets 310, are de-activated and inoperable to register input. One of ordinary skill in the art will understand upon reading this disclosure, the various manner in which selected inputs can be programmed to or configured in an active or inactive state.

As shown in the embodiment of FIG. 3, the one or more physical pages/sheets 310 include one or more printed text sections 314. As shown in the embodiment of FIG. 3, the one or more printed text sections 314 can include questions, including survey questions, and order selections among others. The questions and/or order selections can be associated with yes/no format responses, multiple choice selections and the like. Such questions and/or order selections can take the form of pre-printed text and include blank spaces available for physically writing in questions and/or selections to the one or more physical pages/sheets 310. As shown in the embodiment of FIG. 3, the one or more printed text sections 314 are associated with the array matrix of inputs 311.

The embodiment of FIG. 3, is intended to illustrate that the array matrix of inputs 311 can be embedded and linked, via connections 318, to a switch circuit 320 which can include processor, memory, and other logic, e.g. a microcontroller IC 322. The switch circuit 320 and microcontroller 322 can be further interfaced to an audio chip 323, via connections 325. Embodiments of the present invention include a membrane switch such that the array matrix of inputs can be activated via pressure, resistive, capacitive, and/or induction sensitive elements, among others. The invention is not so limited. In various embodiments, the switch circuit can be powered by a miniature battery or solar cells as represented by the capacitive component 324.

Embodiments of the invention include a connection from the array matrix of inputs 311 to a wireless transceiver 330. The connection is illustrated through the microcontroller 322, via connections 326. As shown in the embodiment of FIG. 3, the selections to the array matrix of inputs 311 can be connected through the integrated circuit of the wireless transceiver 330 to another remote wireless transceiver 350. As shown in the embodiment of FIG. 3, the wireless remote transceiver 350 can be operably interfaced to any number of other remote terminals (including portable remote terminals having printing capabilities), backend computers, servers, workstations, and/or other processing enabled devices. The invention is not so limited.

In the embodiment of FIG. 3, the integrated circuit 330 includes a dual interface radio frequency identification (RFID) chip having a serial contact interface 332 and an RF contact-less interface 338. The serial contact interface is operable to receive signals from the array matrix of inputs 311. In the embodiment of FIG. 3, the serial contact interface 332 is coupled to an access configuration matrix 334. The access configuration matrix 334 is coupled to memory 336. As shown in the embodiment of FIG. 3, memory 336 can include any number of memory types, including but not limited to ROM, RAM, Flash, EEPROM, and so forth. The access configuration matrix 334 is further coupled to the RF contact-less interface 338.

As one of ordinary skill in the art will understand, the technology known as the Radio Frequency Identification (RFID) has the merits of both wireless communication and bar-coding. RFID technology has been used in animal tracking, security cards and inventory/asset management. RFID transponders read and write digital data wirelessly without internal power, drawing power from the radio frequency wave used for data communication. Most common RFID tags use IC chips having only contact-less radio frequency interfaces.

Embodiments of the present invention, can employ a dual interface RFID. For example, a next generation of Smart Cards can have both contact and contactless interfaces to interact with the external world. A dual interface RFID chip can significantly enhance design flexibility. Embodiments of the present invention, utilize a dual interface RFID to facilitate the numerous applications described herein.

Embodiments described herein include methods for questionnaire data automation systems that are based on device and system embodiments as described above. That is, various embodiments combine a dual interface RFID technology and low-profile membrane keypads in a customary human interface format such as would be expected in a traditional setting. Embodiments are supported by application software that can collate, archive and share data with any number of database types based on particular implementations or fields of use. In various embodiments, a device facilitates a surveyed individual to answer formatted questions or enter menu selections with the easiness of button pressing in their own convenient manner. Device embodiments can also allow a user, such as a surveyed individual to enter data, make selections, and/or enter input in a manner which is easier than scanning a bar-code label into computers or computer networks, e.g. easier than the detection mechanism required with a bar code scanner.

As shown in FIG. 3, embodiments of the invention include a wireless electronic survey/order device, e.g. 301. The wireless survey/order device can include one or more page-size, self-contained and low-profile "circuit board(s)", packaged esthetically, and in a customary fashion, for various applications. Device embodiments have a user interface for entering orders and/or selections. Device embodiments also include a wireless interface to other remote terminals or computers to which entered orders and/or selections can be wirelessly communicated for further processing, registration, and/or operation thereupon.

As noted above, FIG. 3 provides one embodiment for the architecture, interface, and electrical components 300 which can be implemented with the present invention. FIG. 3 illustrates an architecture, interface, and electrical components which include in its embodiment one or more "pages" 310 having a low-profile array of input(s) (shown in cutaway view 311) in a customary paper-document size. Switches, 312 and 313, and LCD indicators (not shown) are available next to survey questions and menu contents for users answer selections and order entries. Various graphical designs can be incorporated with the survey questions and contents for promotion and notification purpose.

The embodiment of FIG. 3 further illustrates a microcontroller circuit 320 having processing and memory capability. Thus, the microcontroller circuit 320 can process and store customer data from the array of inputs 311 and convert them into serial digital data, and interface with a dual interface RFID integrated circuit (IC) chip 330. The microcontroller 320 can be powered by a miniaturized battery 324 or solar cells. The invention is not so limited.

As shown in the embodiment of FIG. 3, the dual interface RFID IC chip 330 can include memory 336 which is operable to store customer/user data (selection data) received from the microcontroller 320 and/or other computer executable instructions (instruction sets). The dual interface RFID 330 can also transmit the data through its antenna 340. One of ordinary skill in the art will appreciate the manner in which the antenna 340 can be integrated with an RFID 330 on the same substrate. The antenna 340 can transmit such data to an RF reader/transponder 350, as the same are known and understood by one of ordinary skill in the art. The RFID 330 can receive energy/power and input/output (I/O) commands from the RF reader/transponder 350.

As shown in the embodiment of FIG. 3, the RF reader/transponder is operably connected to a computer 360, which can include a display 362, and/or a computer network. The computer can include a portable wireless terminal as the same has been described herein. The computer 360 can be in a workplace, such as a restaurant, or other particular environment, e.g. school, voting poll location, etc., in which embodiments of the invention are being practiced. As one of ordinary skill in the art will appreciate upon reading this disclosure, application software can be installed in the computer to incorporate response data into the work flow of the particular environment.

Figure 4A:
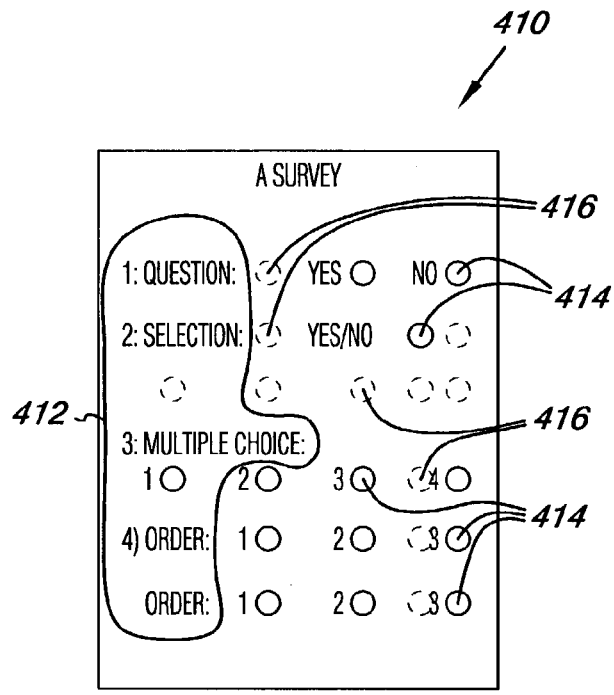
FIG. 4A illustrates an embodiment of a reconfigurable sheet format housing.
Figure 4B:
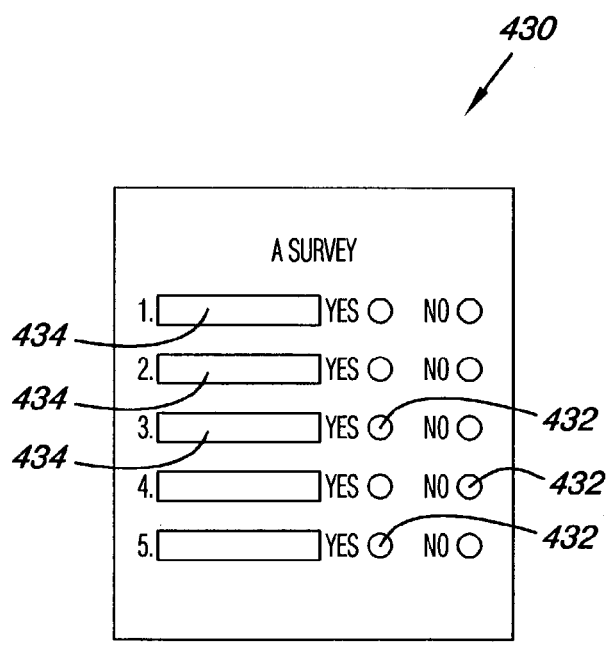
FIG. 4B illustrates another embodiment of a reconfigurable sheet format housing.

FIGS. 4A and 4B illustrate embodiments of a reconfigurable sheet format housing, e.g. one or physical pages/sheets in which an array, and/or matrix, of input components on a substrate can be embedded. The sheet format housing can take the form of a sleeve into which the array, and/or matrix, of input components on a substrate can be inserted. In this manner, the sheet format housing can be readily changed or configured to suit numerous particular applications.

FIG. 4A illustrates one embodiment of a reconfigurable sheet format housing 410. As noted throughout this disclosure, the sheet format housing 410 can be configured and re-configured for different survey protocols or menu changes. In the embodiment of FIG. 4A, the switches in the array of input components (keypads) can be made in a regular matrix and then selectively enabled and/or disabled, e.g. used/activated or left unused/deactivated, to accord with the layout of printed information 412 on the sheet format housing. In other words, the array of input components can be selectively enabled according to particular applications.

Thus, a sheet format housing includes a cover sheet 410 of a graphics design for a specific application which can be printed and applied to (placed over) the array/matrix keypad. As shown in the embodiment of FIG. 4A, needed switches are shown or indicated with locations 414 on the cover sheet 410, while unused switches are covered, as indicated in locations 416.

In various embodiments, all inputs are "live" or enabled such that an actuation, and/or status, of any switch in the matrix will signal the dual interface RFID and be transmitted to a remote terminal/computer (as described above). In these embodiments, application software in a remote terminal/computer (such as 360 in FIG. 3) can be customized to display and use only the information from the switches that are intended, for the specific application. In this way, the electronic hardware of the device can be manufactured in mass production and customized later for specific applications though a cover sheet and application software. In various embodiments, executable instructions (e.g. firmware, or other programs) residing in RFID chips (330) or microprocessors (322) can be modified or reprogrammed, through the contact-less or wireless interface (338) of an RFID, to accept the "live" or enabled input. In various embodiments, executable instructions residing in RFID chips (330) or microprocessors (322) can be modified or reprogrammed, to accept the "live" or enabled input, through the contact interface (332) of an RFID or through input/output (I/O) ports of a microprocessor (322) that can be provided to the portable wireless data device (301).

FIG. 4B illustrates another embodiment of a reconfigurable sheet format housing 430. As in the embodiment of FIG. 4A, the sheet format housing 430 can be configured and re-configured for different survey protocols or menu changes. In the embodiment of FIG. 4B, the switches in the array of input components (keypads) can also be made in a regular matrix and then selectively enabled and/or disabled, e.g. used/activated or left unused/deactivated, to accord with a particular layout on the sheet format housing. Thus, the sheet format housing includes a cover sheet 430 of a graphics design for a specific application which can be printed and applied to (placed over) the array/matrix keypad. And, as shown in the embodiment of FIG. 4B, needed switches can be shown or indicated with locations 432 on the cover sheet 430, while unused switches are covered.

However, the embodiment, of FIG. 4B makes evident that embodiments of the invention provide for "switch white boards" or blank text section spaces 434, in addition to any pre-printed text. The "switch white boards" or blank text section spaces 434, can be provided at any location on the cover sheet 430 as suited to the particular application for which the embodiments 30 are being used. Thus, in the embodiment of FIG. 4B, the "switch white boards" or blank text section spaces 434 are illustrated at the sides of switches. In this manner, the "switch white boards" or blank text section spaces 434 can be filled with particular questions, special items, additional commentary, and the like, at a later time from the point in time in which the cover sheet 430 had earlier printed text added thereto. As shown in FIG. 4B, switches within the embedded input array can be shown or indicated with locations 432 associated with the "switch white boards" or blank text section spaces 434. In various embodiments, text can be physically written into these section spaces 434 and/or labels can be posted/attached thereto.

Figure 5:
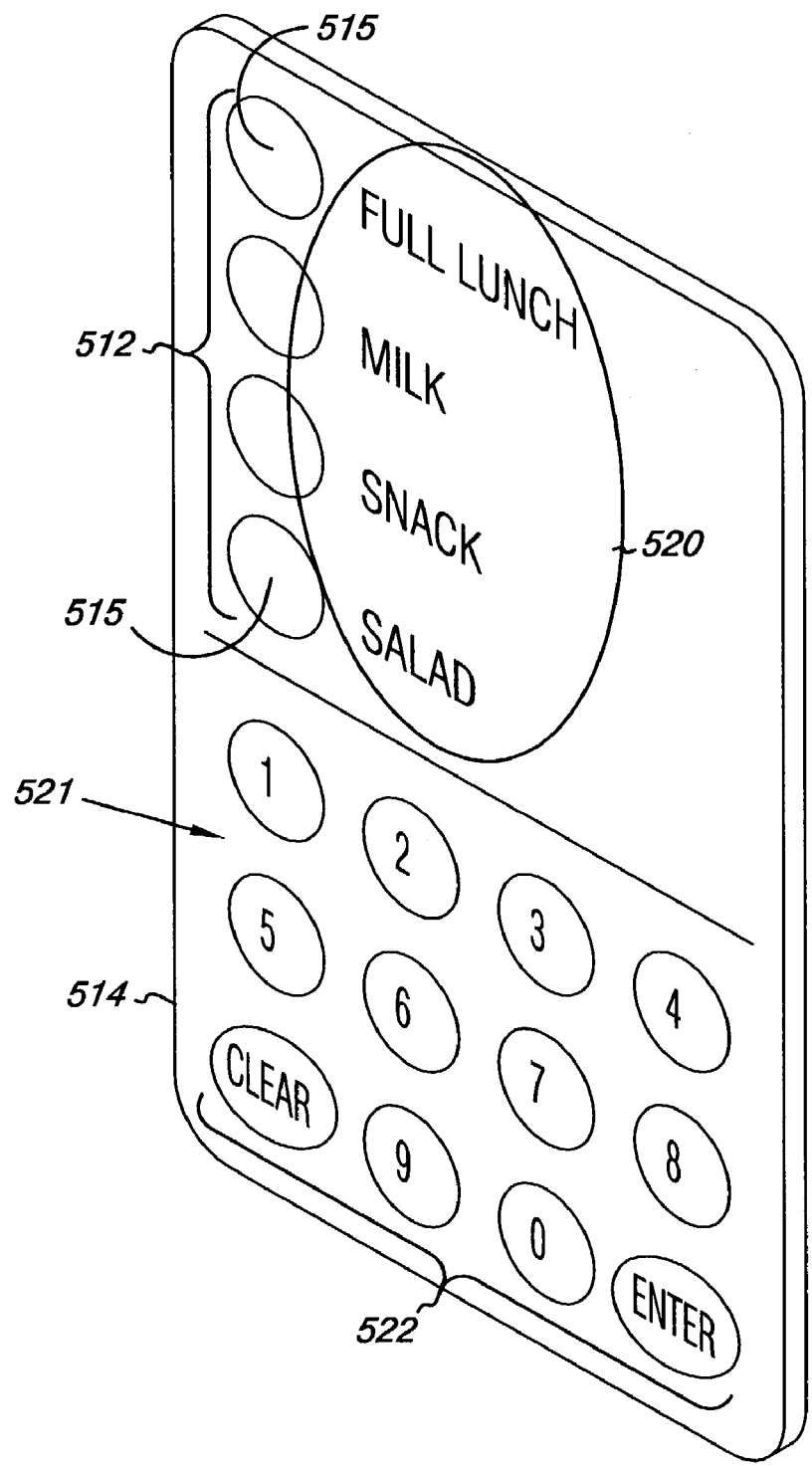
FIG. 5 illustrates an embodiment for another portable wireless data device.

FIG. 5 illustrates an embodiment for another portable wireless data device. The embodiment of FIG. 5, illustrates the use of portable wireless data device embodiments, as described herein, with lockable item and response selections. In this manner, embodiments of the portable wireless data device can be implemented as debit cards, gift cards, meal cards, and/or other pre-selected transactions. As before, text sections 520 and inputs 512 associated therewith can further be associated with one or more visual indicators 515 and/or audio functionality. An input key section 521 can be employed to authenticate a user of the device in "secure" mode. By way of example and not by way of limitation, a recipient of the device can enter, among input keys 522, an appropriate personal identification number (PIN) to validate, transmit, authorize, etc., one or more items among the text sections, e.g. pre-selectable items 520.

By way of example and not by way of limitation, the embodiment of FIG. 5 is being illustrated for use as a third party programmable meal transaction card. The sheet or card format 514 includes an array of embedded inputs 512 associated with one or more text sections 520, as the same have been described herein. In the embodiment of FIG. 5, the sheet or card format 514 illustrates a student lunch card 514 showing having a list of available student meal selections 520. In various embodiments, an amount of credit can be purchased and stored in the device for the selectable items represented as 520 and a PIN can be issued to a recipient. A recipient can then use the card to purchase one or more of the pre-selectable, pre-programmable, items 520 after entering the PIN through input key section 521.

A parent can pre-select order selections 515, e.g. select permissible order choices. As before, text sections 520 and the inputs 512 associated therewith can further be associated with one or more visual indicators 515 and/or audio functionality. The invention is not so limited.

Once the order selection is completed, an input key section 521 can be employed to store and secure the selection. For example, among the input keys 522 shown, an enter key (ENTER) can be employed to store the selection and move to a "secure" operation. In a "secure" operation, a personal identification number (PIN) can be entered such as by using the numbered keys (1, 2, . . . , etc) among the input keys. A recipient of the device can later enter, among the input keys 522, an appropriate PIN to validate, transmit, authorize, etc., the pre-selected order selections 515. One of ordinary of ordinary skill in the art will appreciate the manner in which embodiments can similarly be applied to gift card, and other pre-selected transactions.

As described herein, there are various ways the one or more physical pages/sheets, e.g. cover sheets and/or user interface can be embedded with an array of inputs (switches and/or keypads) and can be integrated with visual indicators, such as LED's. In various embodiments, the switches themselves can be LED-back-lit. In various embodiments, LED's are placed at the side of the switches as indicators of switch status. In various embodiments, letters and/or text, such as YES and NO or other text selections, are placed on top of the switches.

As described herein, the switches can be made of various low-profile switches. Embodiments of the invention include low-profile switches, e.g. membrane switches. One of ordinary skill in the art will appreciate the different substrates, structures and/or materials or which a membrane switch can be made.

It is noted that although RFID chip technology and its industrial standards are discussed in the embodiments presented herein as an example of wireless communication, the invention is not so limited. That is, the scope of the present application is intended to cover other transceiver types and their associated protocols for the device embodiments. Other wireless technology can be use with the methods described here too.

In various embodiments, such as shown in FIG. 2A, two "pages" of the inputs can be placed on two facing cover sheets, each having associated input arrays and respective circuit boards. In this manner, a device embodiment can be "double-sided" in its interior much like the manner in which a customary restaurant menu would be presented.

In various embodiments, audio chips can additionally be embedded with a substrate and interfaced with the array of inputs within the sheet format housing. In various embodiments, the audio chips can be automatically triggered upon some general action upon the sheet format housing, e.g. movement, opening a folded menu, or the like. In various embodiments, the audio chips can be activated by a user of the device, such as upon actuation of a selection input or triggering an input designed to trigger additional voice instructions and/or information. These embodiments can additionally be combined. The invention is not so limited. In this manner, embodiments of the invention are operable to communicate additional information, such as answers, selection feedback, and selection summaries, (e.g. total prices) among other information, back to a user. One of ordinary skill in the art will appreciate that such embodiments can be useful in the context of survey verification, such as with voting selections or menu item ordering. Various embodiments of the invention are operable to detect and notify a user when a conflict of selection entries exists.

Application Embodiments of the Present Invention

Embodiments of the invention described herein provide wireless data transfer using devices the size of normally printed paper forms or restaurant menus. Device embodiments are thin and light enough to be implemented in many settings in which other wireless devices, such as PDAs and/or laptops would be cumbersome and/or inappropriate. Embodiments of the invention, accommodate printed and handwritten text to be posted and/or presented by the device in the same manner as traditional, paper printed forms would be. Therefore, a user can handle and read the printed and handwritten text in the manner as one would handle and read paper forms. Input and selections can be entered by actuating inputs while the device is carried or ported around anywhere and the data transmitted within the wireless network range, thus creating added flexibility. In various embodiments, response entry is completed by actuating a send input. Various selections can be permanently recorded after actuating an input to generate a stop entry signal, and/or upon a specific action, such as when a host/server/attendant (e.g. nurse, receptionist, or casher) passes the device through a radio frequency reader.

By way of example and not by way of limitation, advantages include that the device embodiments accord: 1) a self-explanatory presentation of printed and/or handwritten text, whether survey questions or selection items, which can be posted in the same manner as printed paper forms; 2) a light-weight (non-cumbersome) device in a paper-like physical shape (customary with particular settings); 3) firsthand, rapid data collection which can be wirelessly transmitted to back-end computer(s) or to a larger computer network; and 4) an ease of re-configuration and/or customization as appropriate to different uses, environments, settings, and wireless protocols As earlier mentioned all of the many embodiments can be supported by software (e.g. computer executable instructions) programmed to various particular uses. By way of example and not by way of limitation, these uses include the following, among others. The invention is not so limited.

Food Order Automation

As will be apparent to the reader, device embodiments can be used as restaurant menus. Device embodiments, as described herein, can replace the conventional drive-thru ordering systems of many fast-food restaurants, such as McDonald, Burger King, etc. The device embodiments can resolve confusion and frustration which can occur between customers and cashiers due to poor sound quality in drive thru speakers/receivers and the often noisy environment surrounding drive-thrus.

In method embodiments, a customer could take a device embodiment, as described herein, and use the same to review menu items in his/her vehicle, share with others in the vehicle, enter orders to the device, and wirelessly transmit completed orders. The user could alternatively pass the device including the completed selection to a casher who could further transmit the order into restaurant's computer ordering system. Either way, manual entry of the order is obviated and servers at drive-thrus can be relieved from wearing microphones and earphones. Additionally, customer satisfaction, the speed of ordering, the ergonomics of the work place and operating cost can all be improved.

As one of ordinary skill in the art will appreciate, the method and device embodiments can also be used for counter-ordering at fast-food restaurants or table-ordering in semi-fast food restaurants such as Culver's. In these settings, customers can pick up a device embodiment while they wait in line or after they are seated at their table. The device embodiments allow the customer to select menu items in advance (waiting in line) or at their own pace when seated. This can enhance customers' restaurant experience without adding staff, and can improve restaurant efficiency.

Waiting Room Patient Data Automation

Patient medical history interviews in hospitals and clinics are routine formatted surveys. Conventionally, hospitals and clinics use paper forms with printed questions. The collected information is then either stored in paper files or has to be entered manually entered into electronic databases. Device and method embodiments of the present invention can replace such traditional, non-electronic and/or non-wireless approaches and further lead to a paperless, wire-free working environment. Embodiments of the invention accord patients, staff and/or visitors with the familiarity as exists conventionally, but with an added convenience afforded by the wireless transfer of data.

As Electronic Medical Records (EMR) and/or Computerized Patient Records (RPD) become more widely used, a need for solutions afforded by the present embodiments will increase. Traditional interactions between a patient and healthcare professionals in a clinic or hospital usually take place in three places: a waiting room where medical history or updates are requested, a nurse room where general questions are asked about current health conditions, and a doctor's office where patient-doctor interview is. Device and method embodiments of the present invention can more efficiently collect, transfer and record routine, standard format questions, thus streamlining the entire process.

Electronic Election Ballots

The traditional approach has been for voters to record their candidate selection on paper ballots. Device embodiments can allow voters to operate on a large format ballot but still gain the efficiency of electronically registering their votes. Device embodiments can indicate when a voter's selections conflict.

Market and Public Surveys

Conventional market surveys are often presented in the form of paper questionnaires. Device embodiments can offer respondents a more engaging interface, e.g. through visual indicators and or audio interaction, while still offering a large format information presentation. The device embodiments can facilitate the more efficient recordation and analysis of responses and even provide a respondent with real time feedback.

Gift Cards with Pre-Selections

Device embodiments can be used as pre-selected transaction cards, e.g. gift cards, student lunch cards, etc. having a selection menus added thereto. In various embodiments, the devices can be as small as debit cards. Thus, students can use them to purchase lunches. Likewise, device embodiments can be purchased as gift cards with preferred items pre-selected. As "pre-selected" gift cards, parents can limit their children to purchase "approved" merchandise such as particular "healthy foods" from fast food restaurants and desired and/or "useful" items from department sores. Such pre-selected gift cards can have a more personal touch from the gift giver than a blank gift card but still have a range of freedom for use by the recipient.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the invention. It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the invention includes any other applications in which the above structures and methods are used. Therefore, the scope of various embodiments of the invention should be determined with reference to the appended claims, along with the full range of equivalents to which such claims are entitled.

It is emphasized that the Abstract is provided to comply with 37 C.F.R. §1.72(b) requiring an Abstract that will allow the reader to quickly ascertain the nature of the technical disclosure. It is submitted with the understanding that it will not be used to limit the scope of the claims.

In the foregoing Detailed Description, various features are grouped together in a single embodiment for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A portable wireless data device, comprising:
   one or more printed physical pages;
   an array of inputs embedded in the one or more printed physical pages;
   a wireless transceiver operably coupled to the array of inputs;
   one or more text sections located on a face of the one or more printed physical pages, where at least one text section is associated with an input in the array of inputs; and
   wherein one or more inputs in the array of inputs is intentionally not associated with any text section located on the face of the one or more printed physical pages.

2. The data device of claim 1, wherein the faces of the one or more printed physical pages are readily detachable from the embedded inputs and can be replaced by an other set of faces of printed physical pages to associate new text sections with the array of inputs.

3. The data device of claim 1, wherein the wireless transceiver includes a dual interface radio frequency identification (RFID) chip operably coupled to the array of inputs.

4. The data device of claim 1, wherein the one or more text sections include text selected from the group of restaurant menu items, political office candidates, merchandise items, and medical questions.

5. The data device of claim 1, wherein the device further includes at least one visual indicator associated with an input in the array of inputs.

6. The data device of claim 1, wherein the device further includes an audio chip associated with an input in the array of inputs and operable to provide an audio summary.

7. The data device of claim 1, wherein the one or more text sections include a blank text section in which text can be physically handwritten.

8. The data device of claim 2, wherein one or more input(s) in the array of inputs can be activated and deactivated according to text sections of the printed physical pane currently over the embedded array of selection inputs.

9. The data device of claim 1, wherein the one or more printed physical pages are in the form of a sleeve-like envelope to receive paper sheets having text sections thereon.

10. The data device of claim 1, wherein the device further includes;
a processor operably coupled to the array of inputs and the wireless transceiver;
a memory operably coupled to the processor;
a display; and
a miniature battery power supply.

11. The data device of claim 1, wherein the device further includes an input section having one or more input keys operable for entering an identifier.

12. A wireless information gathering architecture, comprising:
a portable wireless data device, wherein the portable wireless data device includes;
an array of selection inputs within a sheet format housing, wherein the sheet format housing includes one or more sections of restaurant menu item selections as printed text thereon, wherein at least one section of printed text is associated with a selection input, and wherein at least one input in the array of selection inputs is intentionally not associated with any text section of restaurant menu item selections;
a transceiver operably coupled to the array of selection inputs; and
a remote terminal operable to receive radio frequency signals from the transceiver.

13. The architecture of claim 12, wherein the array of selection inputs are provided on a membrane switch substrate within the sheet format housing.

14. The architecture of claim 12, wherein the sheet format housing is a cellulose based housing.

15. The architecture of claim 12, wherein the remote terminal includes a portable remote terminal, wherein the portable remote terminal is further operable to print a receipt of selected restaurant menu items.

16. The architecture of claim 12, wherein the sheet format housing includes at least one area available to physically post labels to be associated with a selection input.

17. The architecture of claim 12, wherein the transceiver is a radio frequency identification (RFID) component.

18. The architecture of claim 17, wherein the RFID includes a dual interface RFID having a contact interface and a wireless interface.

19. The architecture of claim 12, wherein the portable wireless data device includes a foldable format with a first interior face and a second interior face closeable upon one another, and wherein each interior face includes an array of selection inputs within a sheet format housing.

20. The architecture of claim 12, wherein the portable wireless data device further includes an audio functionality and one or more visual indicators associated with the array of selection inputs.

21. The architecture of claim 20, wherein the audio functionality is operable to provide audio information upon actuation of a selection input.

22. A method for wirelessly communicating data, comprising:
embedding an array of selection inputs on a substrate within one or more printed sheets, the one or more printed sheets having text sections thereon associated with at least one of the array of selection inputs, at least one input in the array of selection inputs is intentionally not associated with any text section;
wirelessly transmitting signals representing one or more actuated inputs; and
wirelessly transmitting signals to deactivate and activate at least one input in the array of selection inputs according to text sections of the one or more printed sheets so that the at least one input is intentionally not associated with any text section.

23. The method of claim 22, wherein the method further includes;
interchanging a printed sheet cover over the embedded array of selection inputs; and
reprogramming a software application to register new information in response to new text sections associated with certain selection inputs.

24. The method of claim 22, wherein the method further includes;
interchanging a printed sheet cover over the embedded array of selection inputs; and
reprogramming through a wireless transceiver in response to new information contained in new text sections associated with certain selection inputs.

25. The method of claim 22, wherein the method further includes;
interchanging a printed sheet cover over the embedded array of selection inputs; and
reprogramming a microcontroller associated with the embedded array of selection inputs in response to new text sections associated with certain selection inputs.

26. The method of claim 22, wherein the method further includes illuminating visual indicators on the one or more printed sheets in response to selection input actuation.

27. The method of claim 26, wherein the method further includes providing audio information upon actuation of at least one input.

28. The method of claim 22, wherein wirelessly transmitting signals includes transmitting signals using a dual interface radio identification (RFID) device operably coupled to the one or more inputs.

29. The method of claim 22, wherein the method further includes preventing further actuation of the one or more inputs upon receiving a stop entry signal.

30. The method of claim 22, wherein the method further includes detecting a conflict of selections associated with the array of selection inputs.

31. A computer readable medium having instructions for causing a device to perform a method, comprising:
interfacing an array of selection inputs within a printed sheet format housing, wherein at least one input in the array of selection inputs is intentionally not associated with any text section;

detecting actuation of one or more inputs in the array of selection inputs within the printed sheet format housing;

triggering visual indicators corresponding to the one or more actuated inputs;

wirelessly transmitting signals representing the one or more actuated inputs; and wirelessly transmitting signals to deactivate and activate at least one input in the array of selection inputs according to text sections of the printed sheet format housing so that the at least one input is intentionally not associated with any text section.

32. The medium of claim 31, wherein interfacing an array of selection inputs within a printed sheet format housing includes interfacing an array of selection inputs within a cellulose based housing having one or more text sections thereon.

33. The medium of claim 31, wherein detecting actuation of one or more inputs in an array of selection inputs includes detecting actuation of one or more inputs associated with choices selected from the group of restaurant menu items, medical information, merchandise items, and political candidates.

34. The medium of claim 31, wherein detecting actuation of one or more inputs in an array of selection inputs includes detecting actuation of one or more inputs on a membrane switch substrate.

35. The medium of claim 31, wherein triggering visual indicators corresponding to the one or more actuated inputs includes providing information associated with the one or more actuated inputs to a display.

36. The medium of claim 31, wherein wirelessly transmitting signals representing the one or more actuated inputs includes wirelessly transmitting signals using a dual interface radio identification (RFID) chip operably coupled to the one or more inputs.

37. The medium of claim 31, wherein the medium further includes instructions to provide audio information upon actuation of at least one selection input.

38. The medium of claim 31, wherein the medium further includes instructions to prevent further registration of actuated selection inputs upon receiving a particular entry signal.

* * * * *